United States Patent
Sawa et al.

(10) Patent No.: US 11,981,957 B2
(45) Date of Patent: May 14, 2024

(54) METHODOLOGY TO IDENTIFY BIOMARKERS RELEVANT TO NEURONS IN THE BRAIN BY USING NON-INVASIVE NASAL BIOPSY

(71) Applicant: The Johns Hopkins University, Baltimore, MD (US)

(72) Inventors: Akira Sawa, Baltimore, MD (US); Koko Ishizuka, Baltimore, MD (US); YeeWen Candace Wu, Baltimore, MD (US); Youjin Chung, Amherst, NY (US); Nao J. Gamo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 655 days.

(21) Appl. No.: 16/107,246

(22) Filed: Aug. 21, 2018

(65) Prior Publication Data

US 2019/0078149 A1    Mar. 14, 2019

Related U.S. Application Data

(60) Provisional application No. 62/548,267, filed on Aug. 21, 2017.

(51) Int. Cl.
| | | |
|---|---|---|
| *C12Q 1/6827* | (2018.01) | |
| *A61B 10/02* | (2006.01) | |
| *C12Q 1/6883* | (2018.01) | |
| *G16B 40/10* | (2019.01) | |

(52) U.S. Cl.
CPC ............ *C12Q 1/6827* (2013.01); *A61B 10/02* (2013.01); *C12Q 1/6883* (2013.01); *C12Q 2539/10* (2013.01); *C12Q 2600/106* (2013.01); *C12Q 2600/112* (2013.01); *C12Q 2600/118* (2013.01); *C12Q 2600/156* (2013.01); *C12Q 2600/158* (2013.01); *G16B 40/10* (2019.02)

(58) Field of Classification Search
CPC .. C12Q 1/6883; C12Q 1/6886; C12Q 1/6827; C12Q 2600/106; C12Q 2600/112; C12Q 2600/118; C12Q 2600/156; C12Q 2600/158
See application file for complete search history.

(56) References Cited

U.S. PATENT DOCUMENTS

| | | | |
|---|---|---|---|
| 7,846,676 B2 | 12/2010 | Yang et al. | |
| 9,400,277 B2 | 7/2016 | Yang et al. | |
| 2001/0051344 A1* | 12/2001 | Shalon | B82Y 30/00 |
| | | | 435/6.11 |

OTHER PUBLICATIONS

Kroese et al. (Genetics in Medicine, vol. 6 (2004), p. 475-480).*
Kitchen (Nature Neuroscience, vol. 17, 2014, pp. 1491-1499).*
Narayan et al. (Neuropsychopharmacology, 2013 (38), ACNP, 52nd Annual Conference, T109, p. S339-S340).*
Benitz-King (J. Neuroscience Methods, 2011, vol. 201, pp. 35-45).*
Ishizuka (Schizophrenia, Mar. 2015, vol. 14, Issue Supplement 1, p. 1).*
Borgmann-Winter (Transl Psychiatry, 2015, 5, e527, p. 1-12).*

* cited by examiner

*Primary Examiner* — Sarae L Bausch
(74) *Attorney, Agent, or Firm* — Fox Rothschild LLP

(57) ABSTRACT

Biomarkers relevant to neurons in the brain, in particular at single cell levels, are identified by using olfactory neurons as the best surrogates from subjects so as to establish diagnosis, prognosis, and treatment of brain conditions.

5 Claims, 9 Drawing Sheets
(7 of 9 Drawing Sheet(s) Filed in Color)

METHODOLOGY TO IDENTIFY BIOMARKERS RELEVANT TO NEURONS IN THE BRAIN BY USING NON-INVASIVE NASAL BIOPSY

CROSS REFERENCE TO RELATED APPLICATIONS

This application claims the benefit of U.S. Provisional application 62/548,267 filed on Aug. 21, 2017, the entire contents of which is incorporated herein by reference in its entirety.

FIELD OF THE INVENTION

Embodiments of the invention are directed to the identification of biomarkers relevant to neurons in the brain by using olfactory neurons as the best surrogates from living subjects so as to establish diagnosis, prognosis, and treatment of brain conditions.

BACKGROUND

Dynamic changes in symptom manifestation are prominent in psychiatric and neurological conditions, such as bipolar disorder, schizophrenia, and Alzheimer's disease. Medication intervenes with these dynamic processes. However, the mechanisms of such processes including pathological "state" changes together with "trait" that continuously underlie the disease remain unclear.

Leading stem cell technologies, including induced pluripotent stem cells (iPSCs), allows for the generation of human neuronal cells in a culture dish. A major drawback of this technique is the inability to recapitulate pathological "states" due to genetic reprogramming and prolonged culturing, but "trait" changes can be reasonably depicted.

SUMMARY

Embodiments of the invention are directed to an experimental system that provides molecular snapshots of symptoms and treatment response at the time of biopsy.

In certain embodiments, a method of diagnosing a brain condition or susceptibility to a brain condition in a subject in need thereof, comprises performing a biopsy on the subject to obtain olfactory neurons at the single cell levels or neurons and neuronal cells in culture. Their neuronal identity is validated by the positive expression of OMP or TUBB3 and for the negative expression of non-neural biomarkers comprising HES1, ALDH1A3 or REG3G.

In certain embodiments, a method of diagnosing, providing a prognosis and defining a treatment for a brain condition or susceptibility to a brain condition in a subject in need thereof, comprises obtaining olfactory neurons from a subject, such as, for example, performing a biopsy of a subject's olfactory epithelium to obtain olfactory neurons, profiling biomarkers of single olfactory neuronal cells, comparing the biomarker profile of the subject's olfactory neuronal cells with normal neural biomarker profiling of single olfactory neuronal cells; and, diagnosing, prognosing, and defining the treatment response in the brain condition or susceptibility to a brain condition of the subject.

In one aspect, biomarkers diagnostic of a brain condition are upregulated or down-regulated at the levels of the overall mRNA expression levels, overall protein expression levels, and levels of posttranslational modifications, such as phosphorylation and acetylation thereof as compared to a normal control. In another aspect, the levels of mRNA and/or protein expression and/or the levels of posttranslational modifications in biomarkers in the subject's olfactory neurons are diagnostic and prognostic of a state and/or trait of the subject's brain condition. In another aspect, the identification of biomarker's expression and/or posttranslational modification over time is diagnostic of the subject's state of the brain condition.

In certain embodiments, a method of diagnosing a state and/or trait of a brain condition of a subject comprises obtaining a biological sample from a subject wherein the biological sample comprises olfactory neurons, identifying biomarker profiles of single olfactory neuronal cells, comparing the biomarker profile of single olfactory neuronal cells with biomarker profiles of normal single olfactory neuronal cells; identifying the state and/or trait of the brain condition of the subject, and, administering to the subject identified as having a state and/or trait of the brain condition, a therapeutic agent.

In one embodiment, a brain condition comprises mood dysfunctions, cognitive dysfunctions, psychosis dysfunctions, neurodegenerative dysfunctions, or all psychiatric and/or neurological disorders.

In one embodiment, this novel methodology can apply for any psychiatric and/or neurological disorders.

In certain embodiments, a subset of mood disturbance in the subject is diagnosed by a downregulation of expression of NEUROD1, upregulation of CRMP1, GSK3/β or combinations thereof in the olfactory neuronal cells as compared to a normal control.

In certain embodiments, a subset of cognitive dysfunction is diagnosed by biomarkers comprising Disrupted in Schizophrenia 1 (DISC1), GAPDH, Tau, Aβ42, or combinations thereof. In one aspect, a biomarker, DISC1, is specifically phosphorylated at serine position 713 in the olfactory neuronal cells and/or the GAPDH is acetylated in olfactory neurons and neuronal cells.

In certain embodiments, decreased levels of phosphorylation of DISC1 in olfactory neurons and neuronal cells are predictive of decreased attention function in subjects with psychiatric conditions comprising schizophrenia.

In another embodiment, a subset of psychotic dysfunctions is diagnosed by biomarkers comprising p62. In certain embodiments, the p62 biomarker protein expression in the olfactory neurons and neuronal cells increases as compared to a normal control. In one aspect, increased p62 biomarker expression is diagnostic of psychotic dysfunctions, comprising schizophrenia and bipolar disorder.

In another embodiment, a subset of psychotic dysfunctions is diagnosed by biomarkers comprising IRS2. In certain embodiments, the levels of IRS2 phosphorylation biomarker in olfactory neurons and neuronal cells decreases as compared to a normal control, In one aspect, reduced levels of IRS2 phosphorylation biomarker is diagnostic of psychotic dysfunctions, comprising schizophrenia and bipolar disorder.

In certain embodiments, a method of screening for candidate therapeutic compounds comprises olfactory neurons and neuronal cells in presence or absence of a candidate therapeutic compound; and, detecting the levels of overall mRNA and/or protein, and/or the levels of posttranslational modifications such as phosphorylation and acetylation in olfactory neurons and neuronal cells from a subject having one or more brain conditions as compared to a normal control. In certain embodiments, a candidate therapeutic compound increases or decreases the levels of overall mRNA and/or protein, and/or the levels of posttranslational modifications such as phosphorylation and acetylation in olfactory neurons and neuronal cells from a subject having one or more brain conditions as compared to a normal control, is determinative of a candidate therapeutic compound.

In another embodiment, a method of diagnosing, prognosing and identifying a treatment for a brain condition of a subject comprises performing a biopsy on the subject to obtain olfactory neurons and neuronal cells for molecular profiling approaches at both mRNA and protein levels, including the single-cell molecular profiling for biomarker identification.

Other aspects are described infra.

Definitions

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "agent" or "candidate therapeutic agent" is meant to encompass any molecule, chemical entity, composition, drug, therapeutic agent, chemotherapeutic agent, or biological agent capable of preventing, ameliorating, or treating a dysfunction or other medical condition. The term includes small molecule compounds, antisense oligonucleotides, siRNA reagents, antibodies, antibody fragments bearing epitope recognition sites, such as Fab, Fab', F(ab')$_2$ fragments, Fv fragments, single chain antibodies, antibody mimetics (such as DARPins, affibody molecules, affilins, affitins, anticalins, avimers, fynomers, Kunitz domain peptides and monobodies), peptoids, aptamers; enzymes, peptides organic or inorganic molecules, natural or synthetic compounds and the like. An agent can be assayed in accordance with the methods of the invention at any stage during clinical trials, during pre-trial testing, or following FDA-approval.

By "ameliorate" is meant decrease, suppress, attenuate, diminish, arrest, or stabilize the development or progression of a dysfunction.

As used in this specification and the appended claims, the term "or" is generally employed in its sense including "and/or" unless the content clearly dictates otherwise.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "biomarker" means a distinctive biological or biologically derived indicator of a process, event or condition. Biomarkers can be used in methods of diagnosis, e.g. clinical screening, and prognosis assessment; and in monitoring the results of therapy, for identifying patients most likely to respond to a particular therapeutic treatment, as well as in drug screening and development. Biomarkers and uses thereof are valuable for identification of new drug treatments and for discovery of new targets for drug treatment.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis. The term "predisposition" as used herein means that a subject does not currently present with the dysfunction, but is liable to be affected by the dysfunction in time. Methods of diagnosis according to the invention are useful to confirm the existence of a dysfunction, or predisposition thereto. Methods of diagnosis are also useful in methods for assessment of clinical screening, prognosis, choice of therapy, evaluation of therapeutic benefit, i.e. for drug screening and drug development.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease, dysfunction, or disorder is "alleviated" if the severity of a symptom of the disease or disorder, the frequency with which such a symptom is experienced by a patient, or both, is reduced.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

The terms "pharmaceutically acceptable" (or "pharmacologically acceptable") refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

By "reference" or "normal" is meant a standard or control condition.

As used herein, the term "single cell" refers to an individual cell that has been isolated from other cells. Several methods are useful in isolating single cells, such methods comprising: serial dilution, micromanipulation, laser capture microdissection, FACS, microfluidics, manual picking, and Raman tweezers. For a review, see, for example, D. Ryan et al., *Biomicrofluidics*. 2011 June; 5(2): 021501; Y-C. Chen et al., *Scientific Reports* 6, Article number: 27154 (2016); Y-C Chen et al., *Genome Biology*, 2017, 18:84. In addition, single cell isolation kits are also available commercially (ThermoFisher, Celsee). Single cell isolation allows for "single cell profiling" such as the identification of biomarkers as embodied herein; or gene expression profiles between individual cells; avoid of taking averages of entire cell populations; identify previously undetected subpopulations and the like. Single cell profiling can also be used to quantify a function or property of an individual cell when the interactions of that cell with its environment can be controlled precisely or can be isolated from the function or property under examination.

As used herein, the terms "treat," treating," "treatment," and the like refer to reducing or ameliorating a dysfunction and/or symptoms associated therewith. It will be appreciated that, although not precluded, treating a dysfunction or condition does not require that the disorder, condition or symptoms associated therewith be completely eliminated.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human. The term "gene" is also intended to include variants.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1A:
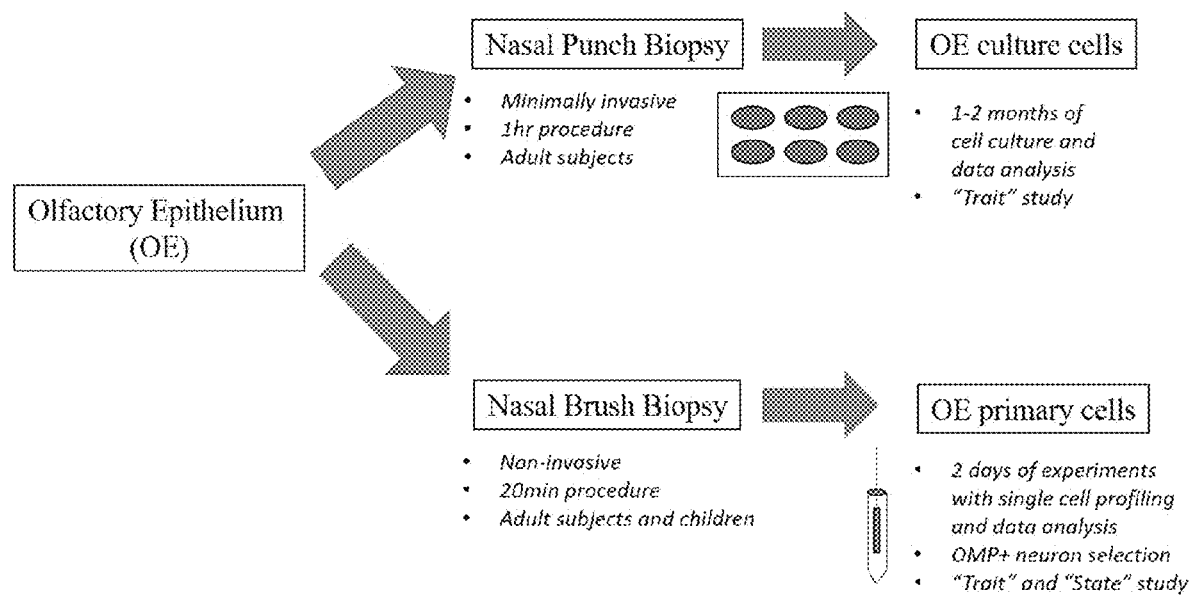
FIG. 1A is a schematic representation of an embodiment of the platform to detect RNA and protein biomarkers that indicate "state" and "trait" in brain conditions using single olfactory neurons collected via nasal brush biopsy or enriched neuronal tissue collected via laser-captured microscopy.

Embodiments of the invention are directed in part, to biomarkers and methods for detecting "state" and "trait" biomarkers for brain conditions, and tracking of state changes over time, in single olfactory neurons. Given that direct brain biopsy cannot be given in daily clinical practice, there was a need to obtain neurons that were the most relevant to estimate biomarkers in neurons inside the brain. Many studies have indicated that the olfactory neurons are non-invasively accessed in daily clinical settings and are the most proximate neurons to the brain neurons in regard to molecular signatures or biomarker viewpoint. Thus, by detecting RNA and protein markers in olfactory neurons at the single cell levels and/or neurons and neuronal cells in culture, from patients, improves diagnosis, prognosis and treatment selection, even prevent disease onset in vulnerable individuals. Moreover, it allows for efficient screening of compounds based on human neuronal biomarkers. In addition, the simple, non-invasive nasal brush biopsy can be performed regularly to monitor disease state and treatment response in younger and older adults, including those who are unstable.

The invention is based, in part on results obtained using a new platform to study brain dysfunctions using neurons derived from the olfactory epithelium (OE). The results established that nasal "brush" biopsy followed by "single cell" molecular profiling directly from biopsied samples was an efficient and accurate method. Multiple groups have traditionally used punch biopsy via nasal endoscope which is still somewhat invasive. In contrast, the brush swab is a 3-minute procedure that is noninvasive and can be performed on children. The cells obtained by this procedure were processed for single cell capture, followed by single cell qPCR on a 96 well plate, single cell RNA sequence, or single cell Western blotting. The neuronal identity is validated by the positive expression of OMP or TUBB3 and for the negative expression of non-neural biomarkers comprising HES1, ALDH1A3 or REG3G. The results showed that 40-70% of cells obtained by the nasal brush swab were neurons and that the number of cells is sufficient for downstream molecular profiling at the single cell level.

The invention embodied herein, presents major advantages over currently available technologies: 1) There are no currently available tools that can measure both "state" and "trait" markers in a cell type that is both easily accessible and relevant to brain conditions. While human neuronal cultured cell lines have been applied to some single-cell techniques, cultured cell lines such as induced pluripotent stem cell-derived neurons and induced neuronal cells do not retain "state" markers, in addition to being prohibitively slow and expensive to use. 2) There is currently no systematic way to use biomarkers to determine diagnosis, prognosis and predict treatment response in patients with brain conditions, and finding the appropriate treatments can take months to years. By using neuronal biomarkers to efficiently determine diagnosis and prognosis and predict treatment response, the technology embodied has the potential to change the way brain conditions are treated and reduce the stigma of mental dysfunctions in society.

In certain embodiments, a method of diagnosing a brain condition in a subject in need thereof, comprises performing a biopsy, for example, a nasal swab, on the subject to obtain olfactory neurons for molecular profiling approaches at both mRNA and protein levels, in particular at the single-cell levels. Biomarker profiles diagnostic of a brain condition are upregulated or down-regulated at the levels of the overall mRNA expression levels, overall protein expression levels, and levels of posttranslational modifications, such as phosphorylation and acetylation, thereof as compared to a normal control. In another aspect, the levels of mRNA and/or protein expression and/or the levels of posttranslational modifications in biomarkers in the subject's olfactory neurons are prognostic of a state and/or trait of the subject's brain condition. In another aspect, the identification of biomarker's expression and/or posttranslational modification over time is diagnostic of the subject's state of the brain condition.

The methods embodied herein are also directed to identifying a state and/or trait of a brain condition of a subject. Accordingly, in certain embodiments, a method of identifying a state and/or trait of a brain condition of a subject comprises performing a biopsy on the subject to obtain olfactory epithelia cells, olfactory neurons for molecular profiling approaches at both mRNA and protein levels, comprising the single-cell molecular profiling for biomarker identification. Biomarkers for a state and/or trait of a brain condition of a subject are upregulated or down-regulated at the levels of the overall mRNA expression levels, overall protein expression levels, and levels of posttranslational modifications, such as phosphorylation and acetylation thereof as compared to a normal control.

The biomarker profiles from the subject, when compared to a normal control, can be upregulated or downregulated at overall mRNA and protein levels, and levels of posttranslational modifications, such as phosphorylation and acetylation, comprising the single-cell profiling. In an aspect of the invention, a panel of biomarkers comprising at least two markers can be correlated with markers from normal neuronal cells. In another aspect, a profile of biomarkers includes, besides an expression profile, a change in state of a marker, e.g. phosphorylation, acetylation, glycosylation etc. of a marker as compared to a normal marker form a healthy control.

In certain embodiments, the levels of mRNA and/or protein expression and/or those of posttranslational modification, such as phosphorylation and acetylation, as biomarkers in the subject's olfactory neurons in particular at the single cell levels, is diagnostic of a state and/or trait of the subject's brain condition. In some embodiments, the identification of the expression of mRNA and/or protein, and/or posttranslational modification of protein, in particular at the single-cell levels, over time is diagnostic of the subject's state of the brain condition.

In certain embodiments, a method of diagnosing, prognosing and identifying a treatment for a brain condition of a subject comprises performing a biopsy on the subject to obtain olfactory neurons for molecular profiling approaches at both mRNA and protein levels, in particular at the single cell levels, for biomarker identification. Biomarkers for a state and/or trait of a brain condition of a subject are upregulated or down-regulated at the levels of the overall mRNA expression levels, overall protein expression levels, and levels of posttranslational modifications, such as phosphorylation and acetylation, thereof as compared to a normal control.

In one embodiment, this novel methodology can apply for any psychiatric and/or neurological disorders.

In embodiments a brain disease or disorder condition comprises mood dysfunctions, cognitive dysfunctions, psychotic dysfunctions, neurodegenerative dysfunctions, or other mental or neurological dysfunctions, or subsets thereof.

In certain embodiments, a subset mood dysfunctions, or subsets thereof, of the subject is diagnosed by a downregulation of expression of NEUROD1, upregulation of CRMP1, GSK3/3 or combinations thereof in the olfactory neurons as compared to a normal control. Examples of mood dysfunctions include, without limitation, bipolar disorder, major depressive disorder, or dysthymia.

In other embodiments, cognitive dysfunctions or subsets thereof, are diagnosed by detecting a biomarker profile comprising DISC1, GAPDH, Tau, Aβ42, or combinations thereof. Examples of a cognitive dysfunction include, without limitation, schizophrenia, of delirium, dementia, learning disorder, traumatic brain injury (TBI), post-traumatic stress disorder (PTSD), obsessive compulsive disorder (OCD), substance dependence disorder (SDD), depression, dementia, Alzheimer's disease, Parkinson's disease, autism, attention deficit disorder (ADD), or attention deficit hyperactivity disorder (ADHD).

In certain embodiments, DISC1 is phosphorylated at serine position 713 in a patient's olfactory neurons at lower levels compared to a normal control. In certain embodiments, the GAPDH is acetylated in the single-cell olfactory neurons derived from a patient at higher levels compared to a normal control. In yet another embodiment the Tau biomarker is differently phosphorylated at threonine at position 231, serine at position 181 in the olfactory neuronal cells as compared to a normal control. Accordingly, in certain embodiments, a biomarker profile of a state and/or trait of a brain condition comprises a combination of marker expression, specific phosphorylation of one or more amino acids of a marker, acetylation etc.

In some embodiments, decreased levels of phosphorylation of DISC1 in olfactory neurons are predictive of decreased attention function in subjects with schizophrenia.

In certain embodiments, psychosis or psychotic condition is diagnosed by biomarkers comprising increased levels of p62 protein. Psychosis is an abnormal condition of the mind that involves a loss of contact with reality. People experiencing psychosis may exhibit personality changes and thought disorder. Depending on its severity, this may be accompanied by unusual or bizarre behavior, as well as difficulty with social interaction and impairment in carrying out daily life activities.

In certain embodiments, psychosis or psychotic dysfunction, or subsets thereof, are diagnosed by biomarkers comprising the levels of phosphorylation in IRS2 protein.

In certain embodiments, the p62 protein expression in olfactory neurons increases in psychotic dysfunction as compared to a normal control as a biomarker. In an embodiment, increased p62 protein expression is diagnostic of psychotic dysfunctions, or subsets thereof.

In certain embodiments, the levels of phosphorylation in IRS2 protein in olfactory neurons decreased as compared to a normal control as a biomarker. In an embodiment, decreased levels of phosphorylation in IRS2 protein are diagnostic of schizophrenia or bipolar disorder with psychosis.

Biomarker expression: The examples section provides details as to how the identification of biomarker profiles in single-cell olfactory neurons can be used to diagnose, provide a prognosis, identify subjects at risk of developing a brain condition, the state of the brain condition, the trait of the brain condition and whether treatment or a proposed treatment would be therapeutically effective in the particular subject with a particular brain condition.

In certain embodiments, a method according to the invention comprises comparing the level of one or more biomarkers and/or total expression levels of mRNA and protein, and/or posttranslational modification such as phosphorylation and acetylation of one or more markers in olfactory neurons at the single-cell levels, taken from a test subject with the level present in one or more samples taken from the test subject prior to commencement of a therapy, and/or one or more samples taken from the test subject at an earlier stage of a therapy. Such methods may comprise detecting a change in the amount of the one or more biomarkers in samples taken on two or more occasions. Methods of the invention are particularly useful in assessment of brain condition therapies.

A method of diagnosis of or monitoring according to the invention may comprise quantifying the one or more biomarkers in a test biological sample, e.g. an isolated single-cell olfactory neurons taken from a test subject and comparing the level of the one or more biomarkers present in the test sample with one or more controls. The control can be selected from a normal control and/or a brain condition control. The control used in a method of the invention can be one or more controls comprising: the level of biomarker found in a normal control sample from a normal subject, a normal biomarker level; a normal biomarker range at mRNA and protein levels, the levels of posttranslational modification, such as phosphorylation state or acetylation state of a biomarker, the level in a sample from a subject with a schizophrenic disorder, bipolar disorder, related psychotic disorder, or a diagnosed predisposition thereto; a schizophrenic disorder marker level, a bipolar disorder marker level, a related psychotic dysfunction marker level, a schizophrenic disorder marker range, a bipolar disorder marker range, a related psychotic dysfunction marker range or combinations thereof.

Biological samples, for example, olfactory neurons, can be taken at intervals over the remaining life, or a part thereof, of a subject. Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an antipsychotic therapy, such as an anti-schizophrenic or anti-bipolar disorder therapy and the like.

Measurement of the level of a biomarker can be performed by any method suitable to identify the amount of the biomarker in a biological sample taken from a patient or a purification of or extract from the sample or a dilution thereof. Measuring the level of a biomarker present in a sample may include determining the concentration of the biomarker present in the sample. Such quantification may be performed directly on the sample, or indirectly on an extract therefrom, or on a dilution thereof. In methods of the invention, in addition to measuring the concentration of the biomarker in a biological sample, such as olfactory neurons, and processed as described in detail in the examples section which follows, the concentration of the biomarker may be tested in a different biological sample taken from the test subject, e.g. CSF, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

Biomarker levels can be measured by one or more methods selected from the group consisting of: spectroscopy methods such as NMR (nuclear magnetic resonance), or mass spectroscopy (MS); SELDI (-TOF), MALDI (-TOF), a 1-D gel-based analysis, a 2-D gel-based analysis, liquid chromatography (e.g. high pressure liquid chromatography (HPLC) or low pressure liquid chromatography (LPLC)), thin-layer chromatography, and LC-MS-based techniques. Appropriate LC MS techniques include ICAT™ (Applied Biosystems, CA, USA), or iTRAQ™ (Applied Biosystems, CA, USA).

Measurement of a biomarker may be performed by a direct or indirect detection method. A biomarker may be detected directly, or indirectly, via interaction with a ligand or ligands, such as an enzyme, binding receptor or transporter protein, antibody, peptide, aptamer, or oligonucleotide, or any synthetic chemical receptor or compound capable of specifically binding the biomarker. The ligand may possess a detectable label, such as a luminescent, fluorescent or radioactive label and/or an affinity tag.

The term "antibody" as used herein includes, but is not limited to: polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

Phosphorylation or other states of the biomarkers as described herein are suitably measured by conventional chemical or enzymatic methods (which may be direct or indirect and or may not be coupled), electrochemical, fluorimetric, luminometric, spectrophotometric, fluorimetric, luminometric, spectrometric, polarimetric, chromatographic (e.g. HPLC) or similar techniques.

For enzymatic methods, consumption of a substrate in the reaction, or generation of a product of the reaction, may be detected, directly or indirectly, as a means of measurement. The biomarkers of the invention are can be detected and measured using mass spectrometry-based techniques; chromatography-based techniques; enzymatic detection systems (by direct or indirect measurements); or using sensors, e.g. with sensor systems with amperometric, potentiometric, conductimetric, impedance, magnetic, optical, acoustic or thermal transducers.

A sensor may incorporate a physical, chemical or biological detection system. An example of a sensor is a biosensor, i.e. a sensor with a biological recognition system, e.g. based on a nucleic acid, such as an oligonucleotide probe or aptamer, or a protein such as an enzyme, binding protein, receptor protein, transporter protein or antibody.

The biosensor may incorporate an immunological method for detection of the biomarker, an electrical, thermal, magnetic, optical (e.g. hologram) or acoustic technologies. Using such biosensors, it is possible to detect the target biomarker at the anticipated concentrations found in biological samples.

Methods of the invention are suitable for clinical screening, assessment of prognosis, monitoring the results of therapy, identifying patients most likely to respond to a particular therapeutic treatment, for drug screening and development, and to assist in identification of new targets for drug treatment. The identification of key biomarkers specific to a disease is central to integration of diagnostic procedures and therapeutic regimes.

Methods of the invention may further comprise one or more assessments to diagnose and/or monitor a psychotic dysfunction in a subject. Assessment may be a clinical assessment, carried out by a clinician in accordance with accepted assessment protocols, e.g. global functioning score (GAF) or SCID, and/or may involve a self-assessment by the subject. Rating scales may be used to assist diagnosis and/or monitoring. GAF and SCID are assessed on the basis of a clinical interview. It is preferred that assessments, such as global functioning score, are made at (i.e. the same day as) or around (i.e. within a few days of) the time of collection of the test biological sample from the subject.

Using predictive biomarkers such as those described herein, appropriate diagnostic tools such as sensors and biosensors can be developed, accordingly, in methods and uses of the invention, detecting and quantifying one or more biomarkers can be performed using a sensor or biosensor.

The sensor or biosensor may incorporate detection methods and systems as described herein for detection of the biomarker. Sensors or biosensors may employ electrical (e.g. amperometric, potentiometric, conductimetric, or impedance detection systems), thermal (e.g. transducers), magnetic, optical (e.g. hologram) or acoustic technologies. In a sensor or biosensor according to the invention the level of one, two, or three biomarkers can be detected by one or more methods selected from: direct, indirect or coupled enzymatic, spectrophotometric, fluorimetric, luminometric, spectrometric, polarimetric and chromatographic techniques. Particularly preferred sensors or biosensors comprise one or more enzymes used directly or indirectly via a mediator, or using a binding, receptor or transporter protein, coupled to an electrical, optical, acoustic, magnetic or thermal transducer. Using such biosensors, it is possible to detect the level of target biomarkers at the anticipated concentrations found in biological samples.

A biomarker of the invention can be detected using a sensor or biosensor incorporating technologies based on "smart" holograms, or high frequency acoustic systems, such systems are particularly amenable to "bar code" or array configurations. In smart hologram sensors (Smart Holograms Ltd, Cambridge, UK), a holographic image is stored in a thin polymer film that is sensitized to react specifically with the biomarker. On exposure, the biomarker reacts with the polymer leading to an alteration in the image displayed by the hologram. The test result read-out can be a change in the optical brightness, image, color and/or position of the image. For qualitative and semi-quantitative applications, a sensor hologram can be read by eye, thus removing the need for detection equipment. A simple color sensor can be used to read the signal when quantitative measurements are required. Opacity or color of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of the biomarker of the invention are coupled, i.e. they combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarker of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarkers of the invention.

Methods involving detection and/or quantification of the biomarker of the invention can be performed using benchtop instruments, or can be incorporated onto disposable, diagnostic or monitoring platforms that can be used in a non-laboratory environment, e.g. in the physician's office or at the patient's bedside. Suitable sensors or biosensors for performing methods of the invention include "credit" cards with optical or acoustic readers. Sensors or biosensors can be configured to allow the data collected to be electronically transmitted to the physician for interpretation and thus can form the basis for e-neuromedicine.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances. For example, an increase in the level of the peptide biomarker in the test sample relative to the level in a previous test sample taken earlier from the same test subject is indicative of a beneficial effect, e.g. stabilization or improvement, of said therapy on the dysfunction, suspected dysfunction or predisposition thereto.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following a brain condition therapy, e.g., an anti-schizophrenic disorder therapy. Samples can be taken at intervals over the remaining life, or a part thereof, of a subject.

Quantifying the amount of the biomarker present in a sample may include determining the concentration of the peptide biomarker present in the sample. Detecting and/or quantifying may be performed directly on the sample, or indirectly on an extract therefrom, or on a dilution thereof.

Detecting and/or quantifying can be performed by any method suitable to identify the presence and/or amount of a specific protein in a biological sample from a patient or a purification of extract of a biological sample or a dilution thereof. In methods of the invention, quantifying may be performed by measuring the concentration of the peptide biomarker in the sample or samples. Detection and/or quantification of peptide biomarkers may be performed by detection of the peptide biomarker or of a fragment thereof, e.g. a fragment with C-terminal truncation, and/or with N-terminal truncation. Fragments are suitably greater than 4 amino acids in length. Preferably, fragments are in the range of from about 6 to about 50 amino acids in length.

The biomarker may be directly detected, e.g. by SELDI or MALDI-TOF. Alternatively, the biomarker may be detected, directly or indirectly, via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag. Ligands include, for example: (1) in vivo: T3, T4 (thyroid hormones), vitamin A (indirectly by interacting with serum retinol-binding protein), apolipoprotein A1 (ApoA1), noradrenaline oxidation products, and pterins. (2) in vitro (most of them pharmacological agents): some non-steroidal anti-inflammatory drugs (NSAIDs), environmental pollutants, such as polyhalogenated biphenyls and thyromimetic compounds, xanthone derivatives as well as natural and synthetic flavonoids.

For example, methods relating to detecting, monitoring, diagnosing and/or quantifying can be performed by one or more methods selected from the group consisting of: SELDI (-TOF), MALDI (-TOF), a 1-D gel-based analysis, a 2-D gel-based analysis, Mass spec (MS), LC and LC-MS-based techniques. Appropriate LC MS techniques include ICAT™ (Applied Biosystems, CA, USA), or iTRAQ™ (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods for diagnosis or monitoring according to the invention may comprise analyzing a biological sample, e.g. cerebrospinal fluid (CSF) or serum, by SELDI-TOF, MALDI-TOF and other methods using mass spectrometry to detect the presence or level of the peptide biomarker. Such techniques may be used for relative and absolute quantification and also to assess the ratio of the biomarker according to the invention with other biomarkers that may be present. These methods are also suitable for clinical screening, prognosis, monitoring the results of therapy, identifying patients most likely to respond to a particular therapeutic treatment, for drug screening and development, and identification of new targets for drug treatment.

Surface-enhanced laser deionization ionization (SELDI) mass spectrometry is a powerful tool for identifying a characteristic "fingerprint" of proteins and peptides in body fluids and tissues for a given condition, e.g. drug treatments and diseases. This technology utilizes protein chips to capture proteins/peptides and a time-of-flight mass spectrometer (tof-MS) to quantitate and calculate the mass of compounds ranging from small molecules and peptides of less than 1,000 Da up to proteins of 500 kDa. Quantifiable differences in protein/peptide patterns can be statistically evaluated using automated computer programs which represent each protein/peptide measured in the biofluid spectrum as a coordinate in multi-dimensional space. This approach has been most successful in the field of clinical biomarker discovery as it can be used as a diagnostic tool without knowing the biomarkers' identity. The SELDI system also has a capability of running hundreds of samples in a single experiment. In addition, all the signals from SELDI mass spectrometry are derived from native proteins/peptides (unlike some other proteomics technologies which require protease digestion), thus directly reflecting the underlying physiology of a given condition.

Detecting and/or quantifying the peptide biomarker may be performed using any method based on immunological, peptide, aptamer or synthetic recognition. For example, the method may involve an antibody, or a fragment thereof capable of specific binding to the peptide biomarker.

When used in a method of identification, the test substance can be a known chemical or pharmaceutical substance, such as, but not limited to, an anti-schizophrenic disorder therapeutic, or a synthetic or natural chemical entity, or a combination of two or more of the aforesaid substances.

Identifying a candidate therapeutic agent substance capable of stimulating, promoting, activating, phosphorylating, dephosphorylating, acetylating, etc. of a biomarker, in a subject, may comprise exposing a test cell to a test substance and monitoring levels or state of the biomarker within the test cell, or secreted by the test cell, e.g. olfactory neuronal cell.

Treatment: In embodiments of the invention, are methods of treating a brain condition, e.g. psychosis, cognitive, mood, or subsets thereof. In one aspect, the method is directed to treating a mood dysfunction. Traditional, known medications can be used and/or any of the agents that may be identified based on the methods embodied herein for diagnosis, prognosis and/or identification of subjects at risk of developing a brain condition and/or candidate agent screening. As used herein, a "mood dysfunction" refers to a disturbance in emotional state, such as is set forth in the Diagnostic and Statistical Manual of Mental Disorders, published by the American Psychiatric Association. Mood dysfunction, or, subsets thereof include but are not limited to major depression, postpartum depression, dysthymia, and bipolar disorder. In one embodiment, the mood disorder is major depression.

Mood dysfunctions as used herein include, but are not limited to, depressive disorders, such as major depressive disorder (MDD), dysthymia and depressive disorder not otherwise specified, and bipolar disorder (or manic-depression). MDD can be further subcategorized as being atypical depression, melancholic depression, psychotic major depression, catatonic depression, postpartum depression and seasonal affective disorder. Depressive disorders not otherwise specified include recurrent brief depression and minor depressive disorder. Bipolar disorder can also be subcategorized into bipolar I, bipolar II, cyclothymia and bipolar disorder not otherwise specified.

In another aspect, the method of treatment is directed to treating neurodegenerative dysfunctions, or subsets thereof. The neurodegenerative dysfunction is selected from the group consisting of AIDS dementia complex, Alzheimer's disease, amyotrophic lateral sclerosis, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Huntington's disease, Kennedy's disease, Krabbe disease, Lyme disease, Machado-Joseph disease, multiple sclerosis, multiple system atrophy, neuroacanthocytosis, Niemann-Pick disease, Parkinson's disease, Pick's disease, primary lateral sclerosis, progressive supranuclear palsy, Refsum disease, Sandhoff disease, diffuse myeloclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome. In one embodiment, the neurodegenerative dysfunction is selected from the group consisting of Alzheimer's disease, amyotrophic lateral sclerosis, Hunton's disease, and Parkinson's disease. In one embodiment, the neurodegenerative dysfunction is Alzheimer's disease.

In another aspect of the invention is a method of improving cognitive function. In one embodiment, the cognitive function is selected from the group consisting of perception, memory, attention, speech comprehension, speech generation, reading comprehension, creation of imagery, learning, and reasoning. In one embodiment, the cognitive function is selected from the group consisting of perception, memory, attention, and reasoning. In one embodiment, the cognitive function is memory.

In another aspect of the invention is a method of treating a cognitive dysfunction, or subsets thereof. In one embodiment, the cognitive dysfunction is selected from the group consisting of delirium, dementia, learning disorder, attention deficit disorder (ADD), and attention deficit hyperactivity disorder (ADHD), traumatic brain injury (TBI), post-traumatic stress disorder (PTSD), obsessive compulsive disorder (OCD), substance dependence disorder (SDD), depression, dementia, Alzheimer's disease, Parkinson's disease, autism, and schizophrenia. In one embodiment, the cognitive dysfunction is a learning disorder.

In another embodiment of the inventions, is that the identification of biomarkers, expression levels, post-translational modifications, etc., can be used to determine a treatment for the specific brain condition. Over time, the biomarkers may vary prompting the medical practitioner to adjust the subject's treatment.

Candidate Therapeutic agents: Candidate therapeutic agents can be screened using any number and types of assays. In certain embodiments, the cells are single-cell olfactory neurons and neuronal cells obtained from subjects have in a brain condition and from normal control subjects.

Typically, in such assays the cells are contacted with a candidate therapeutic agent, such as for example, cDNA, a random peptide library (encoded by nucleic acids), small molecules, synthetic compounds, naturally occurring compounds etc. In cases where the agents comprise a cDNA library, the cDNA library can comprise sense, antisense, full length, and truncated cDNAs. The peptide library is encoded by nucleic acids. The effect of the candidate therapeutic agent on the biomarker expression, glycosylation etc., is then monitored.

In certain embodiments, a method of screening for candidate therapeutic compounds comprises olfactory neurons in presence or absence of a candidate therapeutic compound; and, detecting the levels of overall mRNA and/or protein, and/or the levels of posttranslational modifications such as phosphorylation and acetylation in olfactory neurons from a subject having one or more brain conditions as compared to a normal control. In certain embodiments, a candidate therapeutic compound increases or decreases the levels of overall mRNA and/or protein, and/or the levels of posttranslational modifications such as phosphorylation and acetylation in olfactory neurons from a subject having one or more brain conditions as compared to a normal control, is determinative of a candidate therapeutic compound.

In one embodiment, the candidate therapeutic agent upregulates and normalizes expression of NEUROD1 in the olfactory neurons from a subject having a subset of mood dysfunction. In another embodiment, the candidate therapeutic compound modulates phosphorylation and/or acetylation of one or more markers comprising DISC1, GAPDH, Tau, Aβ42, or combinations thereof, in olfactory neurons from a subject having a cognitive dysfunction. In certain embodiments, a candidate therapeutic compound modulates phosphorylation of DISC1 and/or Tau in the olfactory neurons obtained from a subject having a cognitive dysfunction. In another embodiment, a candidate therapeutic compound modulates acetylation of GAPDH in the olfactory neurons and obtained from a subject having a cognitive dysfunction. In another embodiment, a candidate therapeutic agent increases phosphorylation of DISC1. Decreased levels of phosphorylation of DISC1 in olfactory neurons is predictive of decreased attention function in subjects with schizophrenia.

In one embodiment, a method of identifying therapeutic agents comprises contacting an isolated single-cell olfactory neurons with a candidate therapeutic agent; determining the biomarker expression and/or profile and correlating the biomarker panel and/or profile with a normal control, wherein a drug is identified based on desirable biomarker profiles and/or panels.

In another preferred embodiment, a cell from a patient is isolated and contacted with a candidate therapeutic molecule. The genes, expression products thereof, are monitored to identify which genes or expression products are regulated by the drug.

Candidate agents include numerous chemical classes, though typically they are organic compounds comprising small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Screening of therapeutic agent assays of the invention suitably include, animal models, cell-based systems and non-cell based systems. Preferably, identified genes, variants, fragments, or oligopeptides thereof are used for identifying agents of therapeutic interest, e.g. by screening libraries of compounds or otherwise identifying compounds of interest by any of a variety of drug screening or analysis techniques. The gene, allele, fragment, or oligopeptide thereof employed in such screening may be free in solution, affixed to a solid support, borne on a cell surface, or located intracellularly.

Another technique for drug screening provides for high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with identified genes, or fragments thereof, and washed. Bound molecules are then detected by methods well known in the art. Alternatively, non-neutralizing antibodies can be used to capture the peptide and immobilize it on a solid support.

The methods of screening of the invention comprise using screening assays to identify, from a library of diverse molecules, one or more compounds having a desired activity e.g. histone acetyltransferase activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with isolated cells with modulated receptors, including the appropriate controls.

In one embodiment, screening comprises contacting each cell culture with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

In the high throughput assays of the invention, either soluble or solid state, it is possible to screen up to several thousand different modulators or ligands in a single day. This methodology can be used for proteins in vitro, or for cell-based or membrane-based assays. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100—about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non-covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder. A number of tags and tag binders can be used, based upon known molecular interactions well described in the literature. Similarly, any haptenic or antigenic compound can be used in combination with an appropriate antibody to form a tag/tag binder pair. Thousands of specific antibodies are commercially available and many additional antibodies are described in the literature Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA.* 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA,* 90:6909-6913 (1993)); vinylogous polypeptides (Hagihara, et al., *J. Amer. Chem. Soc.* 114:6568 (1992)); nonpeptidal peptidomimetics with .beta.-D-glucose scaffolding (Hirschmann, et al., *J. Amer. Chem. Soc.*, 114:9217-9218 (1992)); analogous organic syntheses of small compound libraries (Chen, et al., *J. Amer. Chem. Soc.,* 116:2661 (1994)); oligocarbamates (Cho, et al., *Science,* 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539, 083); antibody libraries (see, e.g., Vaughn, et al., *Nature Biotechnology,* 14(3):309-314 (1996) and PCT/US96/ 10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

High throughput screening can be used to measure the effects of drugs on complex molecular events, e.g. regulation of phosphorylation and/or acetylation. Multicolor fluorescence permits multiple targets and cell processes to be assayed in a single screen. Cross-correlation of cellular responses will yield a wealth of information required for target validation and lead optimization.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

This method relies on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, comprising, but not limited to, fluorescently labeled biomolecules such as proteins, phospholipids, RNA and DNA hybridizing probes. Similarly, fluorescent reagents specifically synthesized with particular chemical properties of binding or association have been used as fluorescent reporter molecules (Barak et al., (1997), *J. Biol. Chem.* 272:27497-27500; Southwick et al., (1990), *Cytometry* 11:418-430; Tsien (1989) in *Methods in Cell Biology, Vol. 29* Taylor and Wang (eds.), pp. 127-156). Fluorescently labeled antibodies are particularly useful reporter molecules due to their high degree of specificity for attaching to a single molecular target in a mixture of molecules as complex as a cell or tissue. The luminescent probes can be synthesized within the living cell or can be transported into the cell via several non-mechanical modes comprising diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17-20; Bright et al. (1996), *Cytometry* 24:226-233; McNeil (1989) in *Methods in Cell Biology*, Vol. 29, Taylor and Wang (eds.), pp. 153-173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448-455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405-434; Giuliano and Taylor (1995), *Methods in Neuroscience* 27.1-16). The pH environment of the reporter can be determined (Bright et al. (1989), *J. Cell Biology* 104:1019-1033; Giuliano et al. (1987), *Anal. Biochem.* 167:362-371; Thomas et al. (1979), *Biochemistry* 18:2210-2218). It can be determined whether a reporter having a chelating group is bound to an ion, such as $Ca^{++}$, or not (Bright et al. (1989), In *Methods in Cell Biology*, Vol. 30, Taylor and Wang (eds.), pp. 157-192; Shimoura et al. (1988), *J. of Biochemistry* (Tokyo) 251:405-410; Tsien (1989) In *Methods in Cell Biology*, Vol. 30, Taylor and Wang (eds.), pp. 127-156).

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405-434; Giuliano et al. (1995), *Methods in Neuroscience* 27:1-16).

The whole procedure can be fully automated. For example, sampling of sample materials may be accomplished with a plurality of steps, which include withdrawing a sample from a sample container and delivering at least a portion of the withdrawn sample to test cell culture (e.g., a cell culture wherein gene expression is regulated). Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

The particular label or detectable moiety or tag used in the assay is not a critical aspect of the invention. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Any type of enzyme label can be used as long as they do not interfere with one of the desired outputs of the assay, e.g. expression and/or acylation/deacetylation state etc. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

The invention further provides a substance, e.g. a ligand, identified or identifiable by identification or screening methods or use of the invention. Such substances may be capable of stimulating, promoting or activating, directly or indirectly, the activity of a peptide biomarker, or of stimulating, promoting or activating generation of the peptide biomarker. The term substances includes substances that do not directly bind the peptide biomarker and directly induce expression of the peptide biomarker or promote or activate a function, but instead indirectly induce expression of the peptide biomarker or promote/activate a function of the peptide biomarker, or phosphorylate, acetylate etc. Ligands are also included in the term substances; ligands of the invention (e.g. a natural or synthetic chemical compound, peptide, aptamer, oligonucleotide, antibody or antibody fragment) are capable of binding, preferably specific binding, to a peptide biomarker.

A kit for diagnosing or monitoring a brain condition or predisposition thereto may contain one or more components selected from a ligand specific for a peptide biomarker, a peptide biomarker, controls, reagents, and consumables; optionally together with instructions for use of the kit.

Pharmaceutical Compositions of the Invention

The agents and/or candidate agents that can be identified on the methods described herein can be formulated into pharmaceutical compositions for the treatment of the diseases, dysfunctions and conditions disclosed herein. The language "pharmaceutical composition" includes preparations suitable for administration to mammals, e.g., humans. When the compounds used in the methods of the present disclosure are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue, The preparations of the present disclosure may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above. Generally, intravenous and subcutaneous doses of the compounds of this disclosure for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day.

An effective amount is that amount treats a disease, dysfunction or condition set forth herein.

If desired, the effective daily dose of the active compound may be administered as two, three, four, five, six or more sub-doses administered separately at appropriate intervals throughout the day, optionally, in unit dosage forms.

While it is possible for a compound of the present disclosure to be administered alone, it is preferable to administer the compound as a pharmaceutical composition.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. In addition, the materials, methods, and examples are illustrative only and not intended to be limiting.

Examples

To ascertain the utility and unique advantage of the experimental system described herein, molecular changes involving the Wnt pathway was studied in patients with bipolar disorder compared with matched controls. Data from single cell analysis have been compared to the molecular profile data from olfactory neuronal cultures after the punch biopsy. The data support the hypothesis that the nasal brush procedure combined with single cell analysis allows neuronal selection which is predicted to detect greater and more specific abnormalities in living patients.

Together, this approach is a new tool for the clinical setting and a powerful complement to the well-established iPSC technology in translational brain medicine.

The methods described herein provide tools to detect "state" and "trait" biomarkers for brain conditions, and be able to track state changes over time, in single olfactory neurons. By detecting RNA and protein markers in olfactory neurons from patients, this tool can improve diagnosis, prognosis and treatment selection, even prevent disease onset in vulnerable individuals, and allow efficient screening of compounds based on human neuronal biomarkers. In addition, the simple, non-invasive nasal brush biopsy can be performed regularly to monitor disease state and treatment response in younger and older adults, including those who are unstable.

Figure 1B:
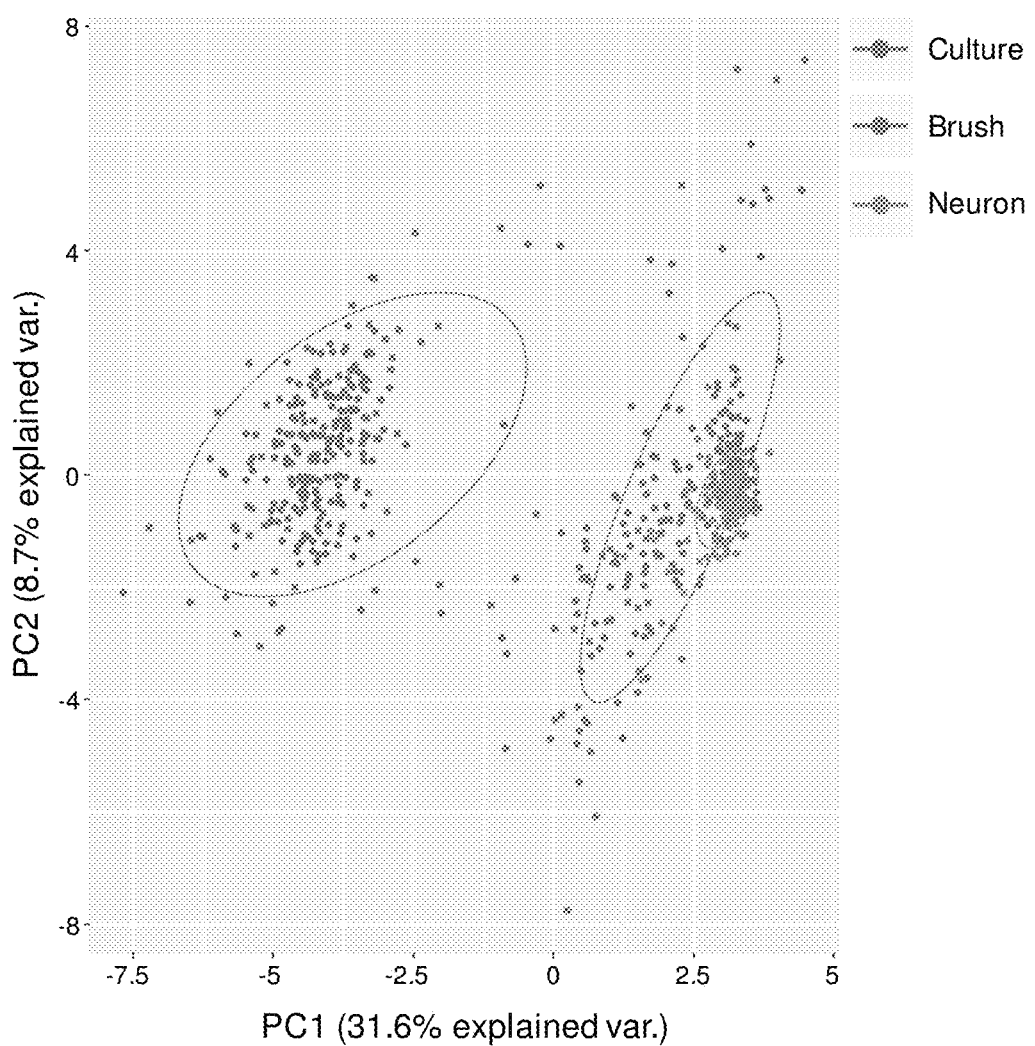
FIG. 1B is a scatter plot showing that the olfactory epithelium contains progenitor cells and olfactory neurons that are continuously regenerated throughout life.

Briefly, the methods herein, detect RNA and protein biomarkers that indicate "state" and "trait" in brain conditions using single olfactory neurons collected via nasal brush biopsy or enriched neuronal tissue collected via laser-captured microscopy (FIG. 1A). The olfactory epithelium, which can be non-invasively biopsied, contains progenitor cells and olfactory neurons that are continuously regenerated throughout life (FIG. 1B).

As a clinical tool, the method can be used to detect a panel of biomarkers in a clinical setting to predict diagnosis, prognosis and appropriate treatments for individual patients with brain conditions, and significantly shorten the time to find effective treatments. It may even be used to identify vulnerable individuals for prevention or early intervention of dysfunction. In addition, the simple, non-invasive nasal brush swab can be performed regularly to monitor dysfunction state and treatment response in younger and older adults, including those who are unstable. As a research tool, the method can be used to screen compounds by measuring neuronal biomarkers associated with dysfunction state or drug response. Including mechanism-guided neuronal biomarkers in clinical trials should dramatically improve the success rate, and contribute to overcoming the "valley of death" during drug development.

Figure 2A:
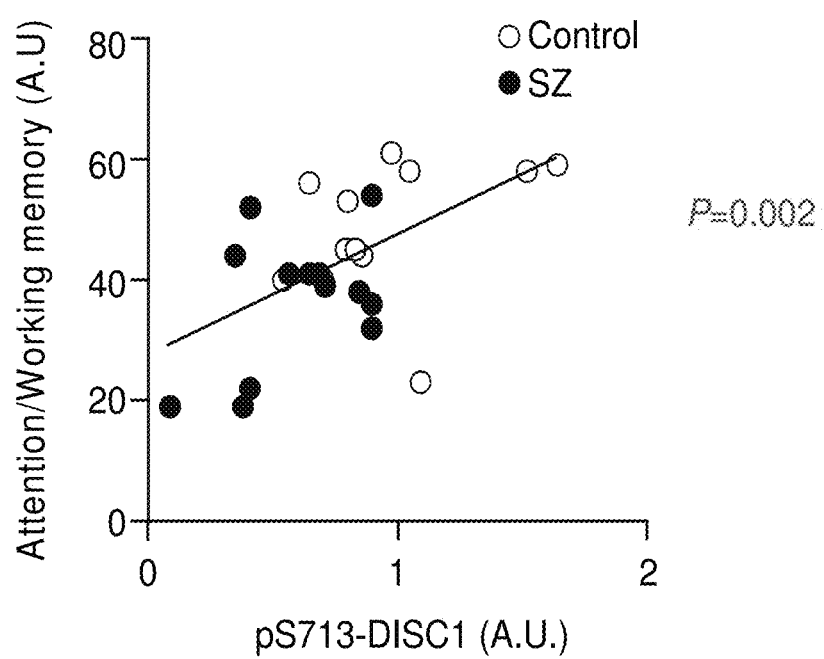
FIG. 2A is a graph showing that specific phosphorylation of the Disrupted in Schizophrenia 1 (DISC1) protein and GAPDH acetylation serve as "trait" markers for cognitive function.
Figure 2B:
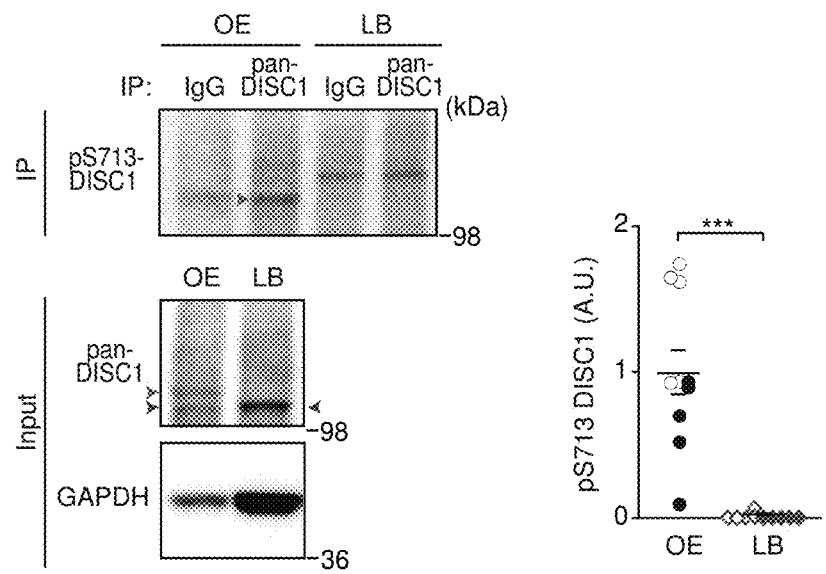
FIG. 2B is a series of blots and a graph showing that DISC1 phosphorylation was not detected in blood lymphoblasts.

Cognition: Specific phosphorylation of the Disrupted in Schizophrenia 1 (DISC1) protein and GAPDH acetylation serve as "trait" markers for cognitive function. Levels of DISC1 phosphorylation at Ser-713 in olfactory neurons predicted worse attention/working memory in controls and patients with schizophrenia (FIG. 2A). Importantly, DISC1 phosphorylation was not detected in blood lymphoblasts (FIG. 2B), necessitating the use of olfactory neurons.

Figure 3A:
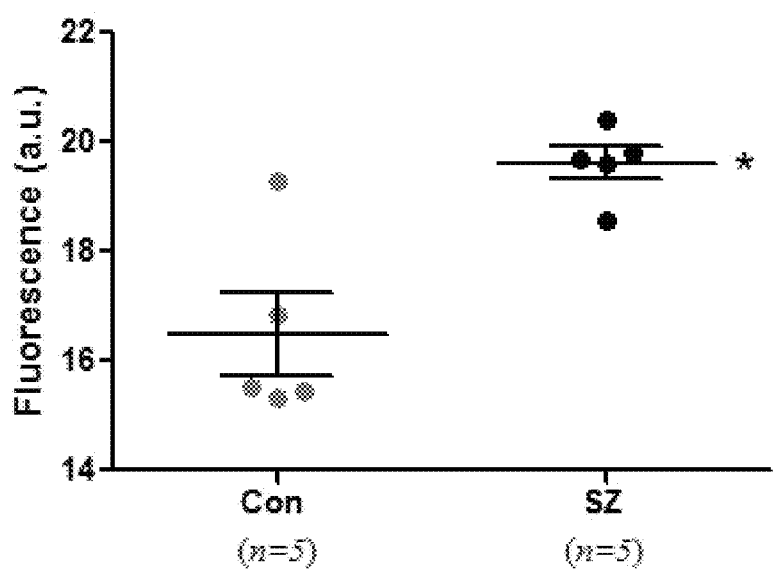
FIG. 3A is a graph showing the autofluorescence was significantly higher in olfactory neurons from patients with schizophrenia relative to control cells.
Figure 3B:
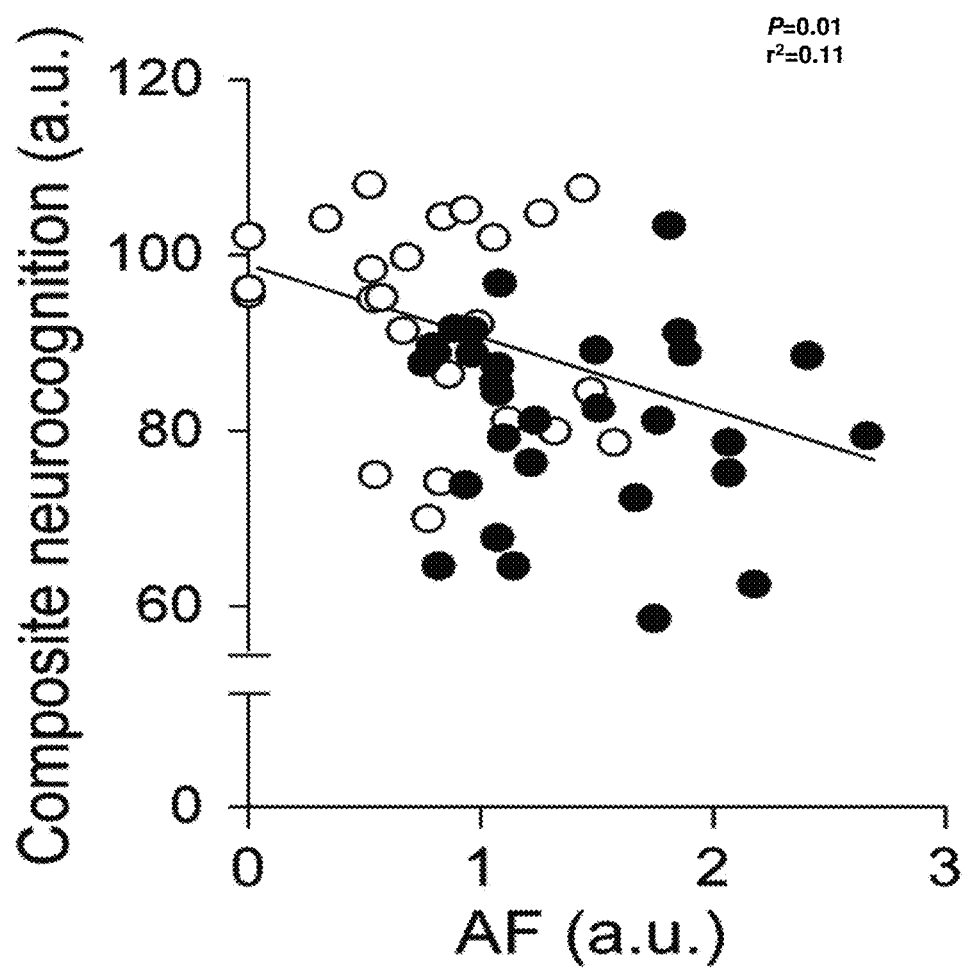
FIG. 3B shows that autofluorescence was negatively correlated with cognitive function.

Oxidative stress initiates a cellular cascade leading to GAPDH acetylation and cellular dysfunction (Sen et al. 2008, *Nat. Cell Biology*), and which is correlated with autofluorescence in cells. Autofluorescence has been found to be significantly higher in olfactory neurons from patients with schizophrenia relative to control cells (FIG. 3A), and negatively correlated with cognitive function (FIG. 3B). While similar results have been obtained from blood lymphoblasts ($p<0.01$), olfactory neurons are much easier and faster to obtain than lymphoblasts, which take 2-3 months to establish.

Furthermore, Tau protein phosphorylated at Thr-231, Ser-181 and A1342 oligomers serve as "trait" markers for Alzheimer's disease diagnosis, and can be detected using the methods herein. It is important to note that phosphorylation of the Tau protein, rather than variations in the tau gene, is associated with disease (Mandelkow & Mandelkow 1998, *Trends in Cell Biol.*; Crawford et al. 1999, *Neurosci. Letters*).

Figure 4:
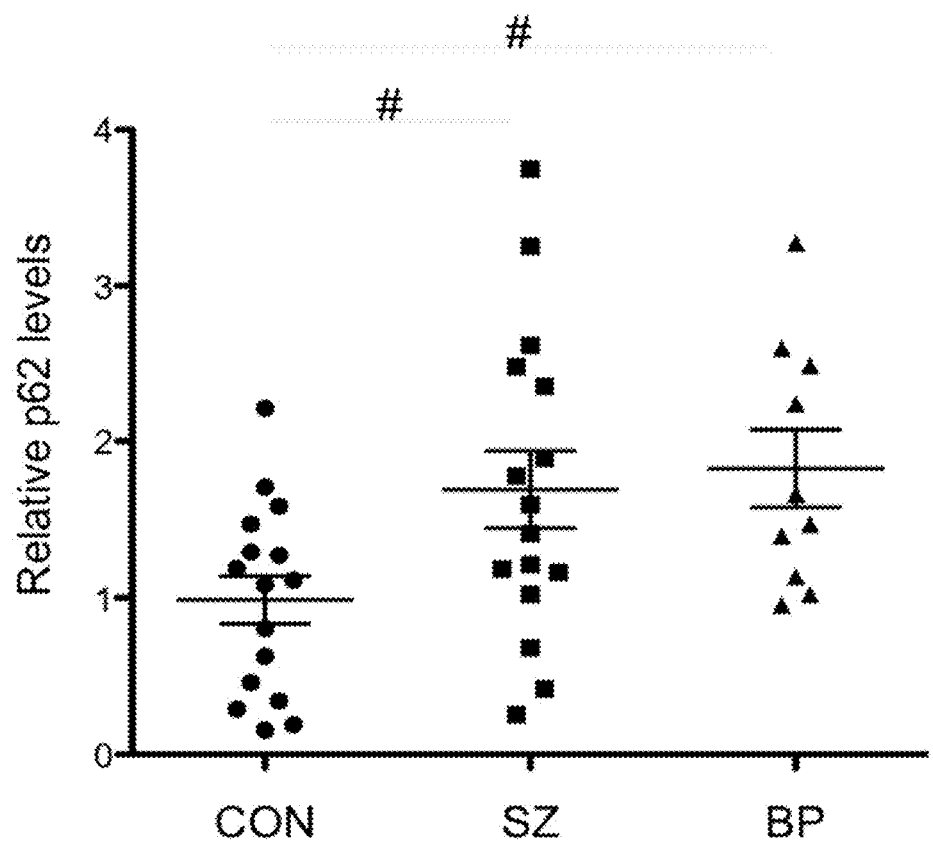
FIG. 4 is a graph showing that p62 accumulation, indicating impaired autophagy, is increased in olfactory neurons from patients with schizophrenia or bipolar disorder with psychosis relative to control cells.

Psychosis: Accumulation of p62 protein serves as a "trait" marker for psychosis. It was found that p62 accumulation, indicating impaired autophagy, is increased in olfactory neurons from patients with schizophrenia or bipolar disorder with psychosis relative to control cells (FIG. 4).

Figure 5A:
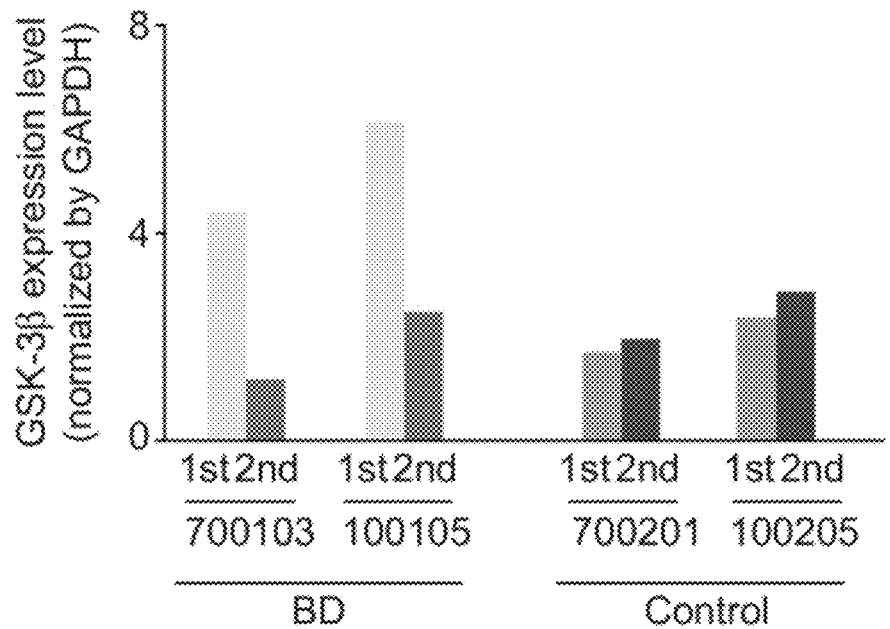
FIG. 5A is a graph showing that GSK3β and CRMP1 gene expression in olfactory neuronal cells serve as "state" markers for lithium response.
Figure 5B:
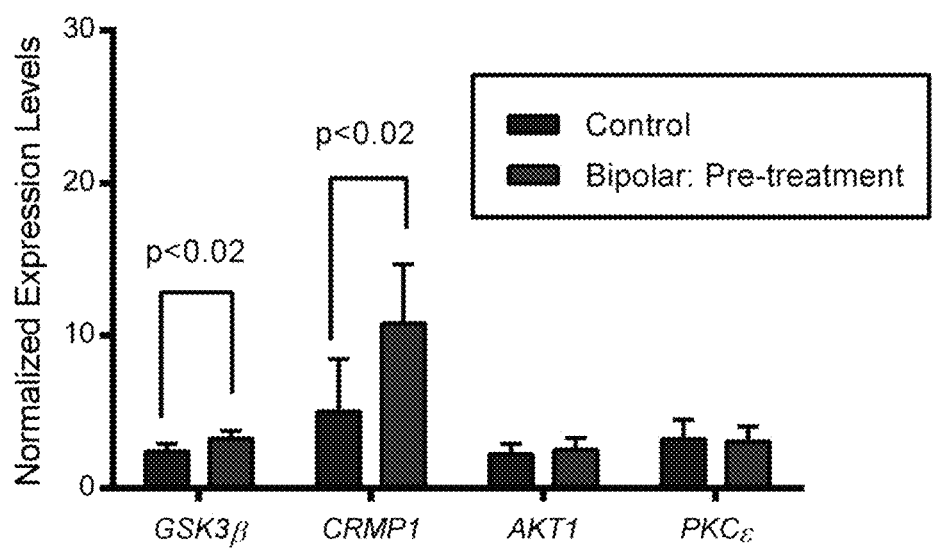
FIG. 5B is a graph showing that CRMP1 as well as GSK31β expression levels were higher in olfactory neurons from BP vs. control cells in a larger number of subjects.
Figure 5C:
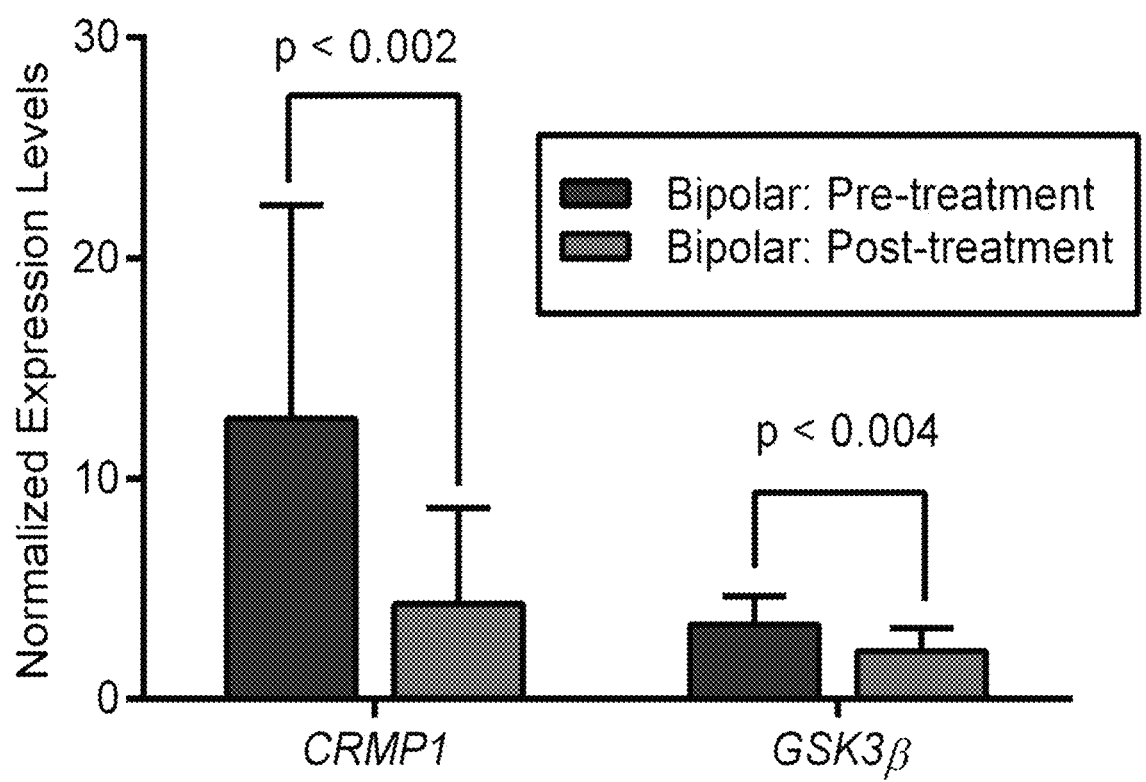
FIGS. 5C and 5D are graphs showing that these expression levels were associated with severity of mood symptoms at baseline, and reduction of gene expression levels in BP cells following 6 weeks of lithium treatment was associated with reduction in depressive and manic symptoms.
Figure 5D:
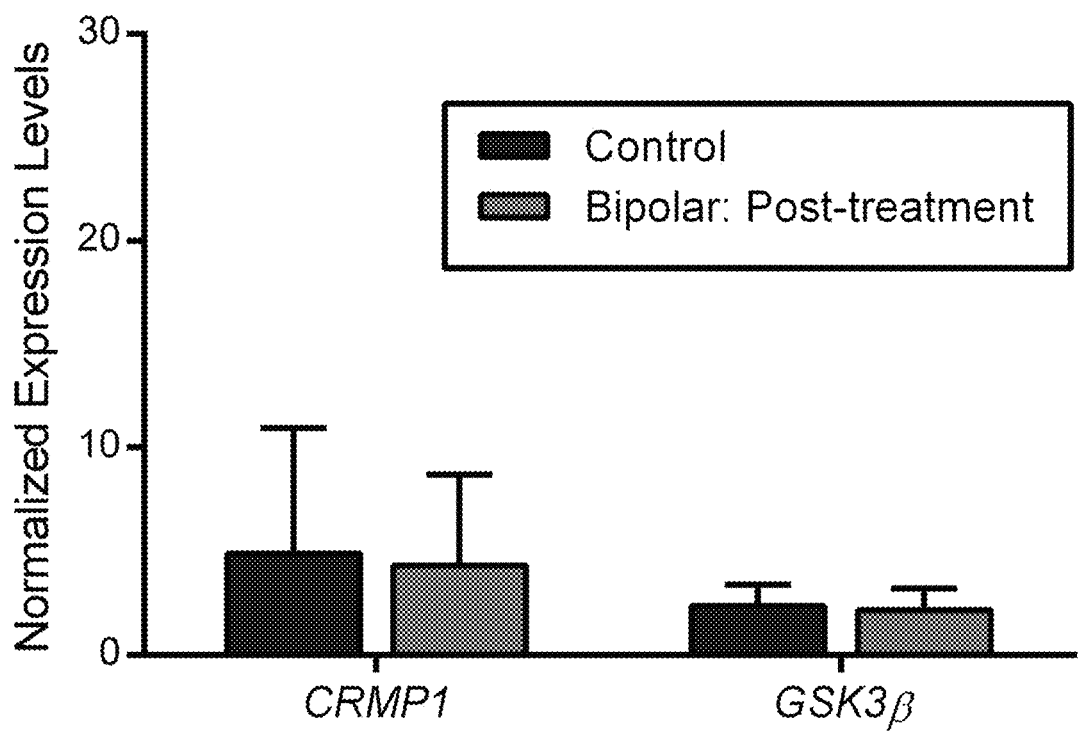

Mood: GSK3β and CRMP1 gene expression in olfactory neuronal cells serve as "state" markers for lithium response. In olfactory neurons, GSK3β expression was higher in bipolar disorder (BP) vs. control cells at baseline, and reduced in BP cells following 6 weeks of lithium treatment (FIG. 5A). CRM1 as well as GSK3β expression levels were found to be higher in olfactory neurons from BP vs. control cells in a larger number of subjects (FIG. 5B). Furthermore, these expression levels were associated with severity of mood symptoms at baseline, and reduction of gene expression levels in BP cells following 6 weeks of lithium treatment was associated with reduction in depressive and manic symptoms (FIGS. 5C, 5D; Tables 1, 2). As studies of GSK3l3 in blood in BP have given mixed results (de Sousa et al. 2015, *J. Psychiatric Res.*; Li et al. 2010, *Bipolar Disorders*; Polter et al. 2010, *Neuropsychopharm.*), the results herein, underscore the value of this technology.

Figure 6:
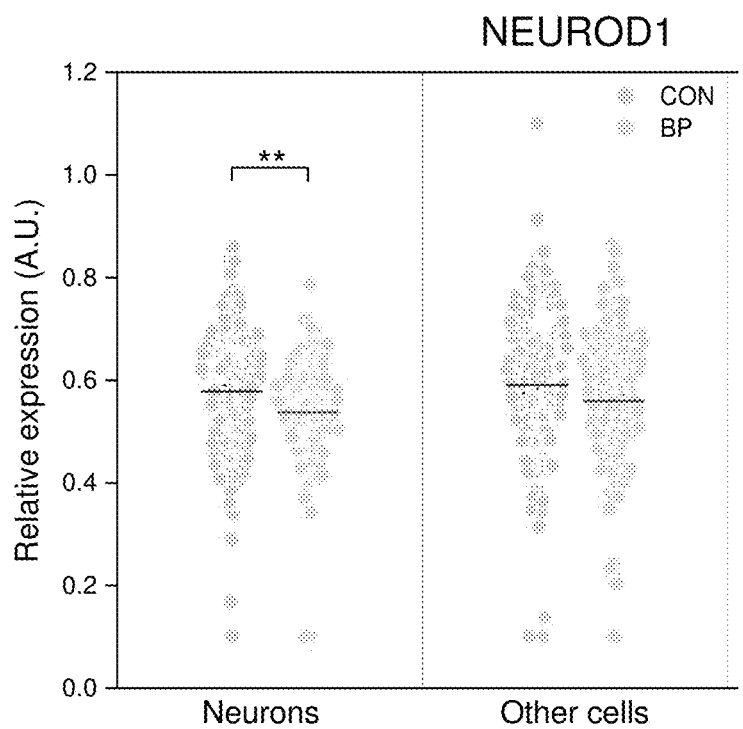
FIG. 6 is a graph showing that NeuroD1 was not expressed in non-neuronal cells from olfactory biopsies, nor in blood lymphoblasts.

Finally, single olfactory neurons from patients with BP with psychosis showed decreased expression of NeuroD1, a transcription factor involved in neurogenesis, relative to control cells. NeuroD1 was not expressed in non-neuronal cells from olfactory biopsies, nor in blood lymphoblasts (FIG. 6).

TABLE 1

Association Between Baseline CRMP1, GSK3β, AKT1, and PKCε mRNA Levels and Severity of Mood Symptoms

|  | YMRS | | | MADRS | | |
|---|---|---|---|---|---|---|
|  | β | 95% CI Text | P | β | 95% CI | P |
| GSK3β (N = 38) | | | | | | |
| Unadjusted[a] | 2.84 | 0.36-5.27 | <0.02 | 0.89 | −2.35-4.14 | <0.60 |
| Adjusted[a,b] | 2.81 | 0.60-5.51 | <0.02 | 0.76 | −2.46-3.99 | <0.70 |
| CRMP1 (N = 35) | | | | | | |
| Unadjusted[a] | 0.45 | 0.11-0.79 | <0.02 | 0.34 | −0.10-0.79 | <0.20 |
| Adjusted[a,b] | 0.48 | 0.13-0.84 | <0.009 | 0.38 | −0.05-0.80 | <0.09 |
| AKT1 (N = 37) | | | | | | |
| Unadjusted | 1.24 | −0.76-3.24 | <0.30 | 1.15 | −1.76-4.06 | <0.30 |
| Adjusted[b] | 1.39 | −0.69-3.47 | <0.20 | 1.35 | −1.66-4.35 | <0.40 |
| PKCε (N = 36) | | | | | | |
| Unadjusted | −0.38 | −1.93-1.17 | <0.70 | −1.1 | −2.42-0.22 | <0.10 |
| Adjusted[b] | −0.25 | −1.72-1.23 | <0.80 | −0.94 | −2.34-0.46 | <0.20 |

CI, confidence interval
[a]Significant association between the baseline normalized expression levels and severity of mood symptoms.
[b]Adjusted for differences in age and sex, and education for all subjects for the different targeted genes.

TABLE 2

Effect of Lithium-Associated Down-Regulation of CRMP1 and GSK3β and Changes in Mood Severity Following Six Weeks of Treatment

|  | YMRS | | | MADRS | | |
|---|---|---|---|---|---|---|
|  | β | 95% CI | P | β | 95% CI | P |
| GSK3β | | | | | | |
| Unadjusted | 2.19 | −0.09-4.28 | <0.05 | −0.61 | −3.11-1.88 | <0.70 |
| Adjusted[†] | 2.43 | −0.44-4.41 | <0.02 | −0.35 | −2.92-2.21 | <0.80 |
| CRMP1 | | | | | | |
| Unadjusted | 0.37 | 0.06-0.68 | <0.02 | 0.42 | 0.03-0.80 | <0.04 |
| Adjusted[†] | 0.36 | 0.06-0.67 | <0.02 | 0.46 | 0.08-0.84 | <0.02 |
| Unadjusted[¥] | 0.54 | 0.15-0.94 | <0.007 | 0.47 | −0.06-1.00 | <0.08 |
| Adjusted[†¥] | 0.51 | 0.15-0.88 | <0.006 | 0.52 | 0.02-1.02 | <0.05 |

[†]Adjusted for differences in age, sex and education.
[¥]Analysis excluded data from BD subjects with undetected CRMP1 mRNA levels

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of diagnosing increased risk of schizophrenia or bipolar disorder in a human subject comprising:
    obtaining single olfactory neurons by a non-invasive brush swab of the subject's olfactory epithelium, wherein neuronal identity is validated by positive expression of OMP;
    analyzing the single olfactory neuron by single cell RNA molecular analysis to determine expression NEUROD1, GSK3β and CRMP1;
    analyzing the single olfactory neuron by single cell molecular analysis to determine phosphorylation of DISC1; and
    detecting a decreased expression of NEUROD1, increased expression of GSK3β and CRMP1, and a decrease of phosphorylation at Serine 713 of DISC1 compared to normal controls; and
    diagnosing the subject with decreased expression of NEUROD1, increased expression of GSK3β and CRMP1, and a decrease of phosphorylation at Serine 713 of DISC1 with increased risk of schizophrenia or bipolar disorder.

2. The method of claim 1, further comprising determining p62 protein expression in the single olfactory neurons.

3. The method of claim 1, further comprising determining phosphorylation of IRS2 protein in the single olfactory neurons.

4. The method of claim 1, wherein increased risk of biopolar disorder is diagnosed.

5. The method of claim 1, wherein increased risk of schizophrenia is diagnosed.

* * * * *